United States Patent [19]

Zacouto

[11] Patent Number: 4,552,150

[45] Date of Patent: Nov. 12, 1985

[54] METHOD AND APPARATUS TO ASSIST CARDIAC MUSCLE FUNCTIONING

[76] Inventor: Fred Zacouto, 16 rue de la Convention, 75015 Paris, France

[21] Appl. No.: 504,170

[22] Filed: Jun. 14, 1983

[51] Int. Cl.$^4$ .............................................. A61N 1/36
[52] U.S. Cl. .............................................. 128/419 PG
[58] Field of Search ...................... 128/419 P, 419 PG

[56] References Cited

U.S. PATENT DOCUMENTS

| | | | |
|---|---|---|---|
| 3,618,615 | 11/1971 | Greatbatch | 128/419 PT |
| 4,181,133 | 1/1980 | Kolenik et al. | 128/419 PG |
| 4,222,386 | 9/1980 | Smolnikov et al. | 128/419 PG |
| 4,303,075 | 12/1981 | Heilman et al. | 128/419 PG |
| 4,406,287 | 9/1983 | Nappholz et al. | 128/419 PG |
| 4,408,606 | 10/1983 | Spurrell et al. | 128/419 PG |
| 4,427,011 | 1/1984 | Spurrell et al. | 128/419 PG |
| 4,429,697 | 2/1984 | Nappholz et al. | 128/419 PG |

FOREIGN PATENT DOCUMENTS 2435954  5/1980  France .......................... 128/419 PG Primary Examiner—William E. Kamm
Assistant Examiner—Mitchell J. Shein
Attorney, Agent, or Firm—Brisebois & Kruger

[57] ABSTRACT

A process for aiding the operation of the heart muscle comprising periodically sending to the heart during at least certain heart cycles sub-threshold test impulses and detecting whether there occurs a systole in response during a time window following the test impulse. In the case of a response, the heart is stimulated at a frequency higher than the heart frequency in course of operation.

23 Claims, 5 Drawing Figures

METHOD AND APPARATUS TO ASSIST CARDIAC MUSCLE FUNCTIONING

The present invention relates to a process and devices for aiding the operation of the heart muscle.

In patients for whom means are provided for aiding the operation of the heart muscle, one of the important problems resides in the adaptation of the operation of these means to the various situations resulting from variations in physiological demands on the circulation or from physiological states of the heart.

Thus, one of the problems encountered consists in adapting an electrical stimulation of the heart to the onset of tachycardia.

In some cases, it is highly desirable to prevent the onset of a tachycardia, for example a ventricular tachycardia the consequences of which may be dangerous, while, in other cases, it is merely desirable to avoid a delayed response to a demand of an increase in the heart output or acceleration of the heart rhythm.

Several methods have already been tried for automatically adapting a frequency stimulating the heart muscle to the physical effort, this in particular in the case of a stimulo-dependent heart.

Thus, it has been attempted to utilize the variations in temperature, the blood pH, the oxygen saturation of the blood, the QT/R-R ratio of the stimulated complexes, all these factors varying in a more or less regular manner and with more or less delay as a function of the physical efforts of a person wearing a pacemaker.

Up to the present time, these various methods have not resulted in truly satisfactory results.

An object of the present invention is therefore to detect preventively a physiological demand of an increase in the heart rhythm and/or of the heart output which cannot be satisfied by the natural means.

Another object of the invention is to detect preventively the onset of a tachycardia, including a ventricular tachyarrhythmia or tacharrhythmia.

Another object of the invention is to adapt a heart rhythm and/or output to a modification and in particular to an increase in the physiological needs.

Another object of the invention is to adapt a stimulation rhythm of a pacemaker to a modification and in particular to an increase in such needs.

Another object of the invention is to prevent the onset of a tachycardia and in particular a ventricular tachycardia.

These objects and others are achieved by a process according to the invention comprising automatically and periodically sending to the heart muscle electrical stimulation impulses of sub-threshold power, current or voltage, i.e. which are insufficient to produce an electro-systole, i.e. a mechanical contraction of the heart muscle, so long as the heart is in its normal physiological situation but sufficient to produce such an electro-systole if the physiological situation of the heart muscle has changed, and detecting the appearance or the non-appearance of this electro-systole during a limited period of time consecutive to the impuse.

These impulses will be termed hereinafter "test impulses". In fact, in most cases, it is sufficient to send such sub-threshold test impulses solely when the rhythm of the heart appears to be normal. Indeed, in the case where for example a tachycardia, or a normally physiological increase in the heart rhythm, has set in, the situation is known and palliative means may be employed if necessary. On the other hand, it has been found, in accordance with the invention, that it is possible to detect in advance, when the operation of the heart appears still normal, a risk of the onset of tachycardia or a modification in the physiological needs as concerns the circulation.

According to an improvement of the invention, the value of the power or current of the sub-threshold electrical test impulse sent out may be adapted to the value of the impedance between the probe carrying the stimulation electrode or electrodes and the heart itself. Normally, this impedance remains constant or varies but slightly, but it is possible to adapt the value of the sub-threshold test impulse.

Preferably, the value of the sub-threshold test impulse, for example in current or duration, is 10 to 85% of the value of a stimulation just sufficient to produce an electro-systolic contraction.

Preferably, the test impulse is always sent out at a given moment of the heart cycle, this moment being preferably included in the second half of the heart cycle. This moment, considered as a percentage of the prior cycle, or measured in duration, may possibly vary along the heart cycle under the effect of sweep control means or vary as a function of the heart frequency so as to be closer to the end of the cycle in the case of high heart frequency.

By way of a modification, a plurality of test impulses may be emitted in succession during the same heart cycle.

As a modification, the moment of the test impulse may vary periodically. For example, it may be for a first cycle at 30% of the heart period; for a second cycle at 50%, etc.; 100% for the eighth cycle and then again at 30% for the ninth cycle, etc.

In another modification, this variation could intervene only periodically during a limited number of cycles within a larger number of cycles.

In a first manner of carrying out the invention in which the basic physiological rhythm corresponding to a situation of rest of the person, is imposed by natural physiological means, the subthreshold test impulse is sent to the heart muscle a little before the probable onset of a spontaneous QRS complex. This may be the case both of a patient in which the production and conduction of the natural electric heart signals are preserved (appearance of the P wave followed by a normal QRS wave or appearance of a normal simple QRS complex) as in the case of a patient suffering from a conduction block and provided with a DDD type sequential stimulator responsive to the spontaneous variation of the P wave and then producing the appearance of a stimulation replacing the defective QRS complex.

In another manner of carrying out the invention, in which the heart is stimulated in a constant manner at a rhythm imposed by a pacemaker, the sub-threshold test impulse is also sent out a little before the sending out of a stimulation impulse.

In the last-mentioned case, it is easy for a pacemaker to establish the moment at which the sub-threshold test impulse must be sent out since it knows the rhythm of its own operation. On the other hand, in the case where one intervenes in accordance with with the invention, in the spontaneous rhythm of the heart, it is possible in a simple way to send the sub-threshold test impulse at the end of a fixed given lapse of time following on a systole or, in accordance with an improvement, the spontaneous heart rhythm may be detected, for example by measuring the duration separating two consecutive spontaneous systoles and, as the case may be, and there may be varied in accordance with the spontaneous rhythm the lapse of time between the systole and the sending of the sub-threshold test impulse, this lapse of time then decreasing when the spontaneous frequency of the heart increases.

As mentioned before, when the heart exceeds a certain rhythm, test impulses may cease to be sent out.

The aforementioned two manners of carrying out the invention may moreover be combined in the case of a heart susceptible to bradycardia and provided with a pacemaker of synchronous type and beating at certain moments spontaneously at a normal rhythm and on the other hand at other moments solely under the effect of a standby stimulation.

In another manner of carrying out the invention, sub-threshold test impulses may be sent to the heart when it beats at a higher rhythm than is normal, for example when it is stimulated at a relavely high rhythm by an anti-tachycardia device stimulating the heart at a high rhythm. In this case, the sending of sub-threshold test impulses may, for example, be employed for checking wether the established anti-tachycardia rhythm is or is not sufficient. In the case where it is sufficient, it can then be attempted to decrease the stimulation rhythm, progressively or in steps, while, if it is insufficient, this rhythm may be increased. In the case of a patient whose heart beats, spontaneously or artificially, at a high rhythm for taking into account an effort or an emotion, the sending of sub-threshold test impulses will enable the presence or the absence of a risk of tachycardia to be checked.

Preferably, the lapse of time between a systole or an electrosystole and the sending of a sub-threshold test impulse is greater than the duration of the refractory and vulnerable zone and preferably between 60 and 90% of the considered heart period.

Preferably, this lapse of time is a fixed proportion, for example between 60 and 90% of the considered heart period, i.e. of the duration between the last two systoles or electro-systoles.

The sub-threshold test impulse is advantageously sent out by an intra-cardiac probe, for example a catheter carrying one or more electrodes.

A sub-threshold test impulse may be sent out after each spontaneous systole or electro-systole, i.e. a sub-threshold test impulse may be sent out per heart cycle, or only a single impulse may be sent out for several cycles. Preferably, at least one sub-threshold test impulse is sent out for a number of cycles between 1 and 100. For example, in the case of a patient subject to tachycardias, it is preferable to send out a test impulse for every cycle or every other cycle or in any case following a small number of cycles whereas, in respect of patients which do not constitute such risks, one impulse every ten or even more cycles would be sufficient.

Also, it is possible, in the last analysis, to avoid considerations of numbers of cycles and to decide to send out a sub-threshold test impulse after a period of a given duration, for example every two or four seconds or every ten seconds, it being understood that once this period of 10 seconds has elapsed, the impulse will only be able to be sent out within a chosen lapse of time which is preferably between 60 and 90% of the period corresponding to the heart rhythm.

The current of the sub-threshold test impulse is preferably between 10 and 85% of the current which is normally just sufficient to produce a contraction, i.e. an electro-systole. As mentioned before, this value depends on the cardiac impedance which may moreover be measured by known means so as to adapt the stimulation to the possible variations of the impedance. As to the value, for a given impedance, of the current which is just sufficient to produce an electro-systole, it may be determined experimentally by progressive variations of the test impulse, or be fixed once and for all after examination and experience of the considered patient.

Preferably, the sub-threshold impulse may have the same voltage as the stimulation impulses but a reduced duration, for example 10 to 50% of the duration of a stimulation impulse, but it would also be possible to employ a different voltage provided there is employed a corresponding duration in accordance with the chronaxia curve (heart threshold variation in relationship to applied voltage and impulse length) of the heart muscle.

According to an improvement of the invention, it is considered that a systole which follows the sending of the test impulse was produced by the latter if the duration between the test impulse and this systole (QRS) is less than a value between 20 and 150 milliseconds.

In other words, a response supervising window is opened whose length is equal to the aforementioned value. In this case, if there occurs within this window an extra systole, the latter is considered as a response to the test impulse even if, in fact, the extra systole was not produced by the test impulse.

According to an improvement of the invention, the detection of such a systole in response to the sending of a sub-threshold test impulse, i.e. the detection of an electro-systole stimulated thereby, may produce the sending of a signal to a monitor in order to enable the nursing personnel to intervene, for example by the administration of a drug.

According to another improvement of the invention, the detection of a response may produce the sending of at least one stimulation impulse at a more rapid rhythm.

In the case of an anti-tachycardia treating device, it is possible, after having detected such a response, to establish an electric stimulation at a high frequency for a certain duration.

In a particularly preferred manner, the detection of a response to the test impulse will produce a moderate increase in the stimulation frequency in a progressive manner or during a step. Thus, for example, there may be envisaged a stimulation per minute and stimulation steps of 60, 70, 80, 90 and 100 stimulations per minute. Thus, if in a patient who is stimulated at the standby rhythm of 50, there is obtained a response to a test impulse, the stimulation rhythm will automatically and immediately assume the value of 60 during for example one minute, then redescend to 50 unless a test impulse during the step of 60 prorduces a response, in which case a new step at 70 is immediately established etc., the absence of response during a step causing, at the end of the step, the frequency to descend preferably to the lower step.

Now if this patient has a spontaneous rhythm of 64 beats per minute (the standby stimulation being then eliminated), and a response to a test impulse is detected, there will be immediately and automatically established a stimulation at the step whose rhythm is just higher than that of the spontaneous rhythm, in the present instance, the step of 70, for one minute.

Instead of effecting a treatment by the sending of a sequence of stimulations at increased frequency, it is possible to act by other means, for example, by an implanted automatic syringe, such as by beta-blocking medicinal preparations.

In another manner of carrying out the invention, the detection of a response may serve to actuate hemodynamic aiding means, for example a heart assistance auxiliary pump acting on a ventriculoaortic, or auriculo-aortic branch.

According to a particular improvement of the invention, the current of the sub-threshold test impulse may be increased when the heart frequency (spontaneous or artificial) increases. The number of cycles between two consecutive sub-threshold stimulation impulses may also be varied.

In a preferred manner of carrying out the invention, there may be measured, during at least a part of the duration of the test impulse, the impedance of the heart, i.e. the impedance between two electrodes used for the stimulation, or a parameter having a relationship with this impedance, for example the electric current passing through an electrode during the test impulse. The impedance may for example be measured between two intracardiac electrodes in the case of the so-called bipolar stimulation or between an intracardiac stimulation electrode and a ground electrode in the case of the so-called monopolar stimulation.

However, the impedance may also be measured during the stimulation impulses. The impedance measurement may be advantageously employed for varying the power, for example the voltage of the test impulse and, possibly of the stimulation impulses, so that the test impulses remain sub-threshold even in the case of a notable drop in the myocardiac excitation threshold.

The periodicity of the sending of the electrical impulses serving to measure the impedance may be situated between the sending of an impulse at each heart cycle and of an impulse for 100 cycles or several hundred cycles, or again in the last analysis it is possible to avoid a number of cycles and decide to send an electrical impulse following on the period of a given duration, for example every two, or four or every ten seconds, it being understood that, once this duration has elapsed, it will only be possible to send the impulse in a chosen period which is preferably between 60 and 100% of the period corresponding to the heart rhythm which is or is not spontaneous.

Likewise, in the case where the electrical impulse is sent out at each cycle of every n heart cycles, this impulse may be sent out in the course of a period of 60 to 100% of the cycle.

This electrical impulse measuring the impedance may be a subthreshold test impulse as seen above, but may also be a sub-threshold impulse which is not used as a test and in this case its power is preferably much lower than the threshold value, for example 5% of the normal threshold value, so as to avoid creating a stimulation. By way of a modification, the impulse could be an electrical stimulation impulse but this solution is not preferred in a pacemaker of synchronous type since the impedance would not be measured in the course of the spontaneous beats.

The measurement of the impedance may advantageously be employed for regulating the power, voltage or duration of the stimulation and/or test impulses, usually by increasing when the impedance increases and decreasing when the impedance decreases.

The means for carrying out the invention will be clear from the following examples which are non-limiting and with reference to the accompanying drawing in which.

DESCRIPTION OF A DETAILED FORM OF THE INVENTION

Figure 1:
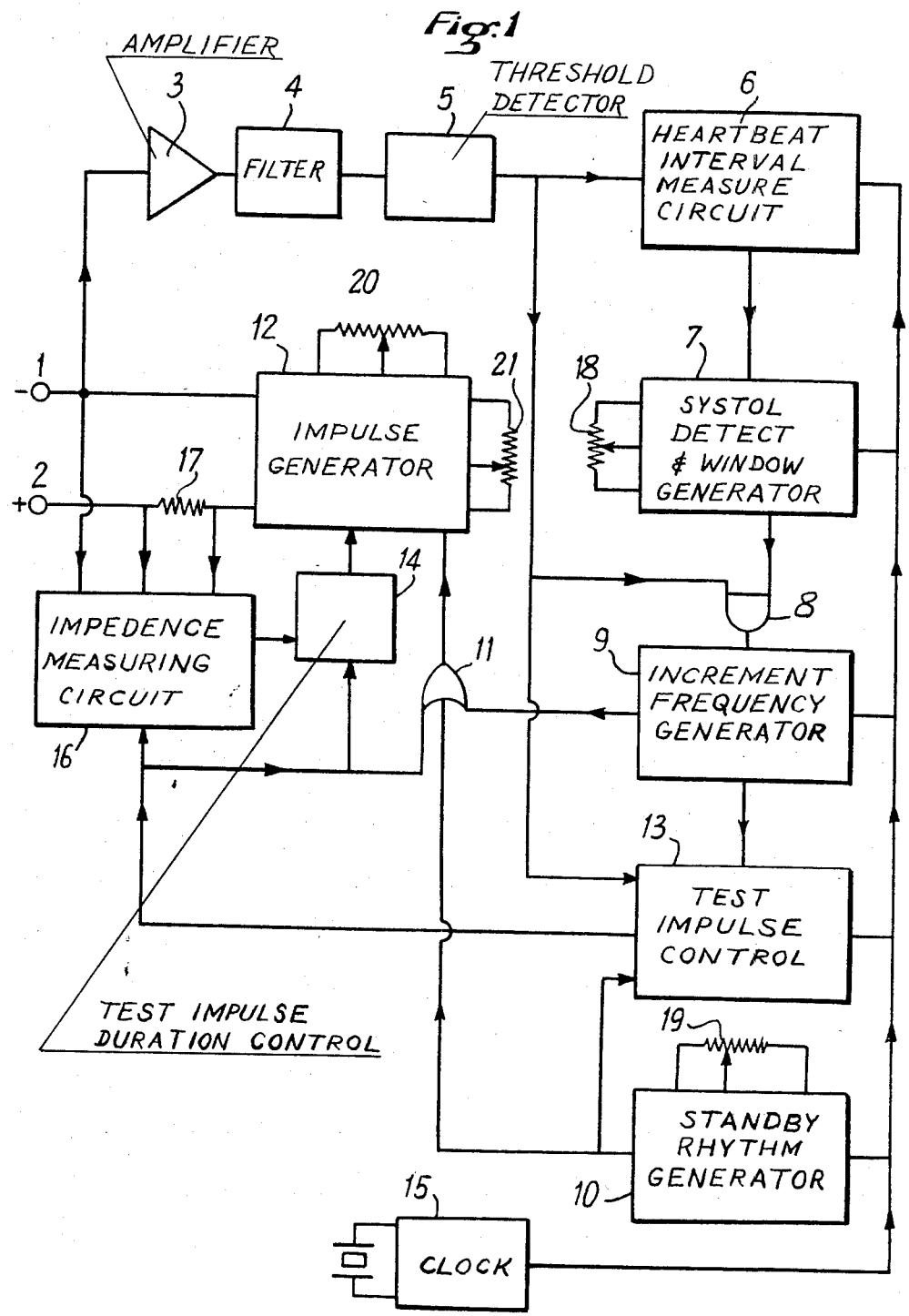
FIG. 1 is a diagram of a pacemaker according to the invention, it being understood that this diagram is in fact formed principally by a microprocessor.

A device according to the invention is incorporated into a pacemaker used on demand (synchronous pacemaker) which is of the ordinary or DDD type. The parts of the pacemaker will not be described since they are well known, except inasmuch as they have a relationship with the invention.

The assembly formed by the device and the pacemaker may be constructed from a microprocessor and its environment, or from a computer, the structure of these apparatus having no need to be described since it is well known to those skilled in the art.

The assembly comprises two electrodes 1, 2 mounted on the same intra-cardiac catheter and both serving to stimulate and detect.

The ventricular stimulation impulses are set at a potential of 2 volts and a duration of 0.5 milliseconds. The threshold excitation of the heart was determined at 1 volt for the same duration of 0.5 milliseconds.

The sub-threshold test impulses always have the same potential of 2 volts but a duration of 0.1 millisecond so that they have a value which is 20% of the value of the stimulation impulses and 40% of said threshold.

The standby frequency of the pacemaker is 50 stimulation impulses per minute. The stimulation increments at increased frequency are 60, 70, 80, 90, 100 stimulations per minute and the duration of an increment is 10 cycles. It is possible to increase the duration of the increment if the increment is solicited several times in a given interval of time.

The device knows the instantaneous frequency of the systoles and electro-systoles, i.e. the duration of each heart cycle which has just finished (interval R—R). On the other hand, the detection is blinded by an electronic field during a period of 30 milliseconds which starts 2 milliseconds before the beginning of the test impulse. The latter is therefore never considered as a systole signal.

A test impulse is sent out every 8 heart cycles after an interval of time of 75% of the length (period) of the preceding cycle. For example, when the cycle is a second (60 beats per minute), the sending out of the test impulse starts 0.750 second after the beginning of the cycle (wave K).

A response detection window W is opened for a duration equal to 100 milliseconds. This window opens at the end of the electronic field. For example, if the cycle is of 1 second, the window is opened 778 milliseconds after the beginning of the cycle and closed at 878 milliseconds after the beginning of the cycle. Any detection during this window is considered as a positive response to the test impulse.

If such a positive response is detected, the frequency increment immediately higher than the spontaneous or electro-stimulated rhythm in process is actuated. At the end of an increment, therefore in the case of absence of positive response to the test impulses, the immediately lower frequency increment is actuated. The operation remains of the "as-required" type during any increment.

Note that if, during an open window, an extra systole which was not produced by the test impulse appears, this extra systole is however considered by the device as a positive response to the test impulse and the immediately higher increment is therefore actuated. The device therefore operates also as a reducer of tachycardia according to U.S. Pat. No. 3,857,399 and according to U.S. Pat. No. 4,052,991 (in particular according to claim 3 in which the predetermined number is equal to 2). However, two distinct windows could also be provided, one for detecting the response to the test impulses and the other for detecting the extra-systoles.

Special cases:

(1) If a positive response is observed during each of the two consecutive cycles, the new increment produced by the first of the two cycles has no time to stimulate and the second higher increment is actuated.

(2) If positive responses are observed during the last increment of 100 stimulations/min, this increment remains actuated for a maximum duration of 300 cycles and then a progressive lowering of frequency increment by increment is produced. The device may also be associated with anti-tachycardia means according to said U.S. patents, which would intervene if the positive responses are observed during the last increment of 100 stimulations per second.

With reference to FIG. 1, there is shown a diagram of the device in question. The latter has two endocardiac electrodes, namely a negative electrode 1 and a positive electrode 2 secured on a catheter (not shown). The electrode 1 is connected to the usual amplifier 3, followed by the usual filter 4, then the usual threshold detector 5 which converts the signals received at the electrode 1 into calibrated impulses provided they have sufficient characteristics. The threshold detector 5 is connected to a time interval measuring circuit 6 capable of measuring the time interval between two successive impulses issuing from the detector 5 and therefore capable of knowing the instantaneous frequency of these impulses. When it has just measured a time interval, the circuit 6 sends a corresponding signal to a circuit 7 recognizing the extra systoles. This circuit sends to an AND gate 8 a 100 millisecond impulse starting, for a cycle, after a delay of 75% of the length of the preceding cycle (measured by the circuit 6). If, during this window, an impulse reaches the detector 5, its output impulse appears on the second input of the gate 8, which sends an impulse to an increment rhythm generator circuit 9.

The standby stimulation is produced by a standby frequency or generator 10, set to produce impulses at the rhythm of 50 impulses/min, and sent to an OR gate 11 whose output pilots a stimulation impulse generator 12 which sends its stimulation impulses to the electrodes 1 and 2, at the rhythm controlled by the impulse generator 10. Further, the standby rhythm generator 10 is responsive, through a path which is not shown but is usual, to the detection impulses issuing from the detector 5. If no impulse leaves the detector 5, the generator 10 operates normally. If an impulse leaves the detector 5, the next impulse produced by the generator 10 is staggered by 1.2 seconds and then re-staggered 1.2 seconds if a new impulse issues from the detector 5, and so on. If the heart beats spontaneously at a rhythm higher than 50/min, the generator therefore remains silent.

A circuit 13 for sequentially controlling test impulses, is also responsive to the standby rhythm generator 10, to the increment frequency or rhythm generator 9 and to the detector 5. It is mentioned that the detector 5, owing to usual means, is not responsive to the electrosignals coming from the stimulation impulses emitted by the generator 12 when the latter is piloted by the generator 10 or the generator 9. The circuit 13 for sequentially controlling the test impulses is therefore responsive to all the stimulation impulses and to all the spontaneous signal impulses passing through the threshold of the detector 5. The circuit 13 emits, every 8 impulses it receives, a test impulse control impulse which is sent to the OR gate 11 and to a circuit 14 controlling the duration of the test impulse. Such a control impulse causes the generation of an impulse by the generator 12 but this impulse only lasts during the period of 0.1 millisecond allowed by the circuit 14, while, if the generator 12 is actuated by the OR gate while the circuit 14 is silent, it generates a stimulation impulse having a length of 0.5 millisecond.

The increment rhythm generator 9, each time it is actuated by the AND gate 8, emits 10 increment impulses toward the OR gate 11. The frequency of these impulses depends on the state of a decoder belonging to the circuit 9 and responsive to the AND gate. The decoder may assume the following states: 0, 1, 2, 3, 4, 5 respectively corresponding to the rhythms 0, 60, 70, 80, 90, 100. If the decoder is in the state 0, it sends no impulse. If it is in any state n different from 0, it sends 10 impulses of corresponding frequency to the OR gate, then returns to the state n−1. If, in a state n different from 5, it receives an impulse from the AND gate 8, it immediately changes to the state n+1. If, in state 5, it receives an impulse from the AND gate 8, it remains in the state 5 for 10 further cycles and so on during a maximum number of cycles equal to 300. When the 300th cycle is reached, it descends to the state 4 where it remains for 300 cycles, then to the state 3, etc., then it remains in or rises to the state in which it counted the smallest number of impulses from the AND gate.

The various circuits 6, 7, 8, 9, 10 are actuated by a high frequency time base or clock 15. It must also be noted that the detection by the threshold detector 5 is prevented after each stimulation impulse or each detection for a duration equal to 40% of the length of the preceding cycle so as to take into account the refractory period of the heart.

In an improved modification, the impulses issuing from the circuit 13 for sequentially controlling test impulses are also sent to an impedance measuring circuit 16 which, on one hand, is connected to the electrode 1 and, on the other hand, measures the strength of the current on the resistor 17 through which the test impulse passes. The circuit 16 is moreover responsive to the voltage of the test impulse so that it can calculate the impedance between the electrodes 1 and 2. If the impedance varies, the circuit 16 acts on the control of the test impulse duration circuit 14 so as to vary this duration as a function of the measured impedance. Preferably, the measurement of the impedance is only effected during a first fraction of the duration of the test impulse so that it can subsequently modify the remainder of this duration if the impedance has varied since the preceding measurement. The circuit 16 operates if, and only if, it is actuated by the circuit 13.

Also seen in the diagram of FIG. 1 are a number of regulating potentiometers which may be actuated manually or by remote control:

18 permits the regulation, in percentage of a cycle duration, the moment or instant of the sending of the test impulse (for example 75%);

19 permits the regulation of the standby rhythm or frequency;

20 permits the regulation of the voltage of the stimulation impulses and the test impulses;

21 permits the regulation of the duration of the stimulation impulses.

The electronic clamp means and the refractory period locking means have not been shown.

The operation is also seen in the other Figures.

Figure 2:
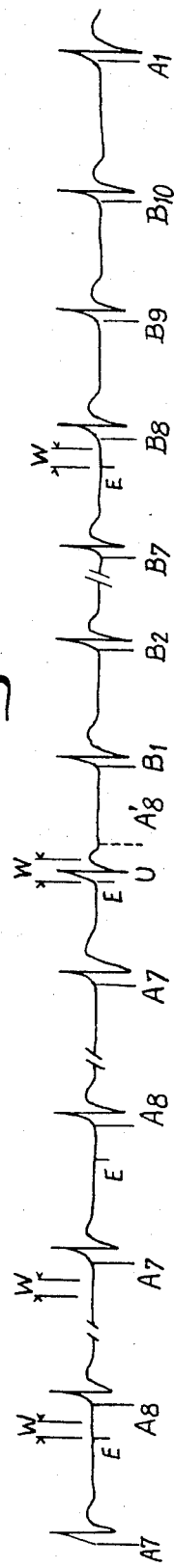
FIGS. 2 to 5 show electrocardiograms showing the operation of the pacemaker.

In FIG. 2, there is seen the detection at the amplifier 3 concerning a bradycardiac patient whose heart is stimulated by stimulation impulses at the frequency of 50/min piloted by the standby rhythm generator 10. The impulses are designated by $A_1 \ldots A_2 \ldots A_7, A_8$ for designating successions of 8 cycles. Each eighth cycle, a sub-threshold test impulse E is emitted followed by the window W. It can be seen that the third test impulse E is followed by a response signal U indicating a contraction during the window W so that the AND gate 8 emits an impulse. The decoder changes from the state 0 to the state 1 and stimulation impulses B1 to B7 are sent out at a frequency of 60/min. After B7, i.e. at the eighth cycle, a test impulse E is emitted, followed by no response. Then arrive the last two impulses $B_9$ and $B_{10}$ of the increment 60/min. The decoder returns to the state 0 and the standby stimulation $A_1 \ldots$ etc. resumes its action.

Figure 3:
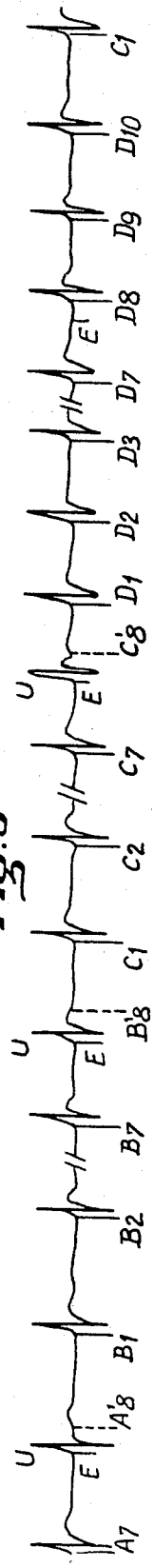

It can be seen from FIG. 3 that an impulse E is followed by a response U in the window W so that the stimulation A'8 has not occurred. The decoder changes to the state 1. After B7, the test impulse E produces a new response U in the window W. The decoder changes to state 2 and eliminates $B'_8, B'_9, B'_{10}$. This time the circuit stimulates at the frequency 70/min. After the seventh stimulation C7 a new response U occurs. The decoder changes to the state 3 and the stimulation increment 80/min starts. After the seventh stimulation D7 the test impulse 6 no longer produces a response so that the last stimulations of the increment $D_8, D_9, D_{10}$ are allowed, after which the decoder changes to state 2, etc.

Figure 4:
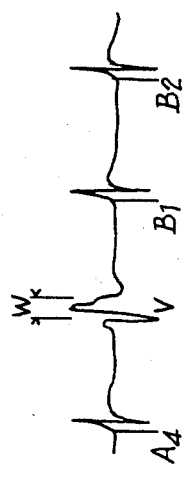

It can be seen from FIG. 4 that, while the window W of a fifth cycle (devoid of a test impulse) is opened, a ventricular extra systole V is detected. This extra systole produces an impulse actuating the rhythm generator 9 whose decoder changes from state 0 to state 1 and produces the stimulation $B_1, B_2 \ldots$ of the 60/min increment.

Figure 5:
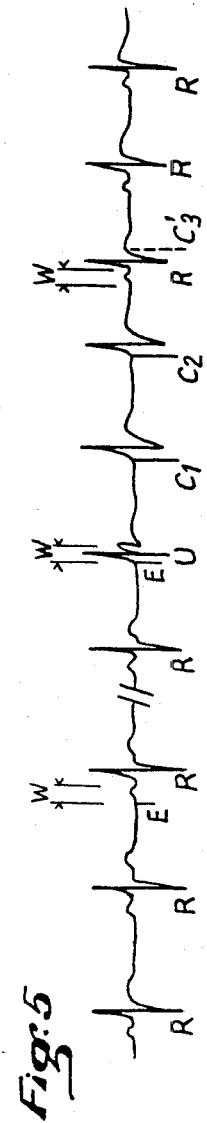

FIG. 5 shows a spontaneous heart rhythm R, R, R . . . at a frequency of 62/min. For each eighth cycle, a test impulse E is produced. One of the impulses is followed by a response U in the window W which produces an impulse issuing from the AND gate. The rhythm generator 9 is therefore actuated. But in this case, the decoder immediately changes to state 2 and produces a stimulation $C_1, C_2$ at the increment 70/min which is just greater than the spontaneous frequency of 62/min. This may be obtained by rendering the decoder responsive to a heart frequency measuring circuit, for example the circuit 6 which puts and maintains the decoder in the state just lower than the measured spontaneous frequency. In the present case, this state was state 1 and the impulse of the AND gate therefore produces the passage to state 2. Thus, the stimulation is effective at the increment just higher than the preceding spontaneous activity.

FIG. 5 also shows that a spontaneous systole R occurring after the window W of the cycle starting with $C_2$, does not increase the stimulation rhythm. $C'_3$ is eliminated and, as the spontaneous rhythm R, R, R is higher than 70/min, the stimulation at increment 70/min is inhibited. In other words, at each increment, the device operates as a pacemaker operating as demanded. However, the state 2 of the decoder remains operative during the entire duration of this spontaneous activity. If the frequency of this spontaneous activity decreases, for example becomes equal to 68/min, the decoder changes to the immediately lower state 1.

In the example described hereinbefore, it is understood that a supervision window W is established for each cycle including the 7 cycles devoid of test impulses. However, a window could also be opened only after the test impulse. A window would also be opened before the test impulse, above all if it is decided to send out the test impulse rather late in the cycle.

I claim:

1. A process for aiding the operation of the heart muscle comprising sensing the heart cycles of the heart, automatically and periodically sending to the heart muscle at a moment before the expected end of a heart cycle, electrical sub-threshold test impulses of a value insufficient to normally produce an electro-systole so long as the heart threshold is greater than a predetermined value, but sufficient to produce an electro-systole if the physiological state of the heart muscle has charged and decreased to a threshold below said predetermined value, and detecting the occurence or nonoccurence of this electro-systole during a limited time window consecutive to the impulse and ending before the expected end of said heart cycle.

2. A process according to claim 1, wherein the value of the test impulses is between 10 and 85% of the threshold value just sufficient to produce an electrosystole when the heart threshold is greater than the predetermined value.

3. A process according to claim 1, wherein at least one test impulse is sent out at a given moment of a heart cycle corresponding to a given percentage of the expected length of the cycle.

4. A process according to claim 3, wherein said moment is separated from the beginning of said cycle by a duration of between 60 and 90% of the length of the preceding cycle.

5. A process according to claim 4, wherein the duration of the limited time window is between 20 and 150 milliseconds.

6. A process according to claim 3, wherein a test impulse is sent out only during certain heart cycles, and wherein the limited time window is provided during all heart cycles.

7. A process according to claim 6 wherein, upon detection of a systole during the limited time window, at least one electrical stimulation impulse is sent out at a frequency which is more rapid than the heart frequency.

8. A process according to claim 1, wherein the moment during a cycle when a test impulse is sent out varies with different cycles.

9. A process according to claim 1, wherein the test impulse is sent out at least once per 100 cycles.

10. A process according to claim 9, wherein the test impulse is sent out in each cycle.

11. A process according to claim 9, wherein the test impulse is sent out once every n cycles, is which n is between 1 and 10.

12. A process according to claim 1, further comprising sending to the heart electrical stimulation impulses constantly or on demand and wherein the duration of the test impulse is between 10 and 50% of the duration of the stimulation impulse.

13. A process according to claim 1, further comprising sending to the heart at least one electrical stimulation impulse, at a frequency higher than the heart frequency, in response to detection of a systole within said limited time window.

14. A process according to claim 13, wherein the increase in the stimulation frequency is relatively small.

15. A process according to claim 14, wherein stimulation increments of increased frequency are provided so long as systoles are detected during the limited time window.

16. A process according to claim 15, wherein, when a last increment, having the greatest frequency, is reached and systoles are detected during the limited time window, the stimulation frequency is decreased after a predetermined time.

17. A processs according to claim 1, further comprising measuring the impedance of the heart during the sending out of impulses and changing the value of the impulses in response to the measure changes in impedance.

18. A device for aiding the operation of the heart muscle, comprising:
  detecting and sensing means for detecting heart systoles and sensing heart cycles,
  means for producing electrical stimulation pulses for the heart muscle,
  means responsive to said detecting and sensing means for sending out electrical stimulation impulses at a standby rhythm in the absence of detection of spontaneous heart systoles,
  means responsive to said detecting and sensing means for sending out electrical sub-threshold test impulses periodically to the heart muscle at a moment occuring before the expected end of a heart cycle,
  means for opening in the heart cycle a supervision window for the systoles at least after each test impulse, said window being closed before the expected end of the heart cycle,
  and means responsive to a detected systole during said window for sending out stimulation impulses at a frequency higher than the frequency of the heart rhythm.

19. A process according to claim 1 wherein, after having detected a systole during said window, a medicinal preparation is delivered by automatic delivering means.

20. A process according to claim 18, wherein said value is increased when the impedance increases and decreased when the impedance decreases.

21. In an anti-tachycardia pacemaker comprising means for stimulating at an increased frequency responsive to means for detecting tachycardia, the improvement comprising means for generating and sending out periodic electrical sub-threshold test impulses, means for detecting a systole occuring during a predetermined supervision window after each test impulse, and means for increasing the frequency of the stimulating means in response to detection of a systole during said predetermined supervision window.

22. A device for aiding the operation of the heart muscle, comprising:
  detecting and sensing means for detecting heart systoles and sensing heart cycles,
  means for producing electrical stimulation pulses for the heart muscle,
  means responsive to said detecting and sensing means for sending out electrical stimulation impulses at a standby rhythm in the absence of detection of spontaneous heart systoles,
  means for generating and sending an electrical sub-threshold test impulse to the heart muscle at least once for every 1 to 100 heart cycles, at a moment occuring before the expected end of a heart cycle,
  means for opening in the heart cycle a supervision window for the systoles at least after each test impulse, said window being closed before the expected end of the heart cycle,
  and means responsive to a detected systole during said window for sending out stimulation impulses at a frequency higher than the frequency of the heart rhythm.

23. A device according to claim 22 wherein said electrical sub-threshold test impulse is sent to the heart muscle by the generating and sending means, at least once for every eight heart cycles.

* * * * *